US008124370B2

(12) United States Patent
Sanders et al.

(10) Patent No.: US 8,124,370 B2
(45) Date of Patent: Feb. 28, 2012

(54) CATIONIC ANTI-MICROBIAL PEPTIDES AND METHODS OF USE THEREOF

(75) Inventors: Mitchell C. Sanders, West Boylston, MA (US); Gerard J. Colpas, Holden, MA (US); Shite Sebastian, Somerville, MA (US); Diane Ellis-Busby, Lancaster, MA (US)

(73) Assignee: Systagenix Wound Management (US), Inc., Wilmington, DE (US)

( * ) Notice: Subject to any disclaimer, the term of this patent is extended or adjusted under 35 U.S.C. 154(b) by 0 days.

(21) Appl. No.: 10/543,523

(22) PCT Filed: Jan. 30, 2004

(86) PCT No.: PCT/US2004/002636
§ 371 (c)(1),
(2), (4) Date: Apr. 20, 2006

(87) PCT Pub. No.: WO2005/012556
PCT Pub. Date: Oct. 2, 2005

(65) Prior Publication Data
US 2006/0240507 A1    Oct. 26, 2006

Related U.S. Application Data

(60) Provisional application No. 60/444,521, filed on Jan. 31, 2003.

(51) Int. Cl.
*C12Q 1/37* (2006.01)
(52) U.S. Cl. ........................................................ 435/23
(58) Field of Classification Search .................... None
See application file for complete search history.

(56) References Cited

U.S. PATENT DOCUMENTS

| | | | |
|---|---|---|---|
| 4,242,447 A | 12/1980 | Findl et al. | |
| 4,259,442 A | 3/1981 | Gayral | |
| 5,210,022 A | 5/1993 | Roth et al. | |
| 5,236,827 A | 8/1993 | Sussman et al. | |
| 5,518,894 A | 5/1996 | Berg | |
| 5,618,675 A * | 4/1997 | Larrick et al. | 435/7.1 |
| 5,811,252 A | 9/1998 | Verheijen | |
| 6,649,365 B1 | 11/2003 | Orenga | |
| 2002/0055101 A1 | 5/2002 | Bergeron et al. | |
| 2005/0142622 A1 | 6/2005 | Sanders et al. | |

FOREIGN PATENT DOCUMENTS

| | | |
|---|---|---|
| EP | 0 122 028 A1 | 10/1984 |
| EP | 0 430 608 A1 | 6/1991 |
| EP | 0 864 864 A1 | 9/1998 |
| JP | 11178567 | 7/1999 |
| JP | 2000093195 | 4/2000 |
| JP | 2001169799 | 6/2001 |
| JP | 2001299381 | 10/2001 |
| WO | WO 97/28261 A1 | 8/1997 |
| WO | WO 00/08203 A1 | 2/2000 |
| WO | WO 02/06821 A2 | 1/2002 |
| WO | WO 02/10433 A2 | 2/2002 |
| WO | WO 03/063693 A2 | 8/2003 |
| WO | WO 2004/087942 | 10/2004 |
| WO | WO 2005/012556 | 2/2005 |
| WO | WO 2005/042770 | 5/2005 |
| WO | WO 2005/042771 | 5/2005 |

OTHER PUBLICATIONS

Thwaite et al. (Antimicrob. Agents Chemo., 50:2316-2322, 2006).*
Murakami et al. (J. Immunol., 172:3070-3077, 2004).*
Bucki et al. (J. Antimocrob. Chemo., 62:329-335, 2008).*
Bergsson et al. (J. Immunol., 183:543-551, 2009).*
BBC News, Health, "Smart bandage 'spots infection'," [online] Nov. 5, 2001 [retrieved on Dec. 28, 2004] Retrieved from the Internet <URL: http://news.bbc.co.uk/1/hi/health/1634639.stm.
Gallo, R. L., et al., "Biology and clinical relevance of naturally occurring antimicrobial peptides," *J. Allergy Clin. Immunol.*, 110(6): 823-831 (2002).
Gottesman S., "Proteases and Their Targets in *Escherichia coli*," Annu. Rev. Genet. 30: 465-506 (1996).
Molla, A., et al., "Degradation of Protease Inhibitors, Immunoglobulins, and Other Serum Proteins by *Serratia* Protease and Its Toxicity to Fibroblasts in Culture," *Infectioin and Immunity*, 53(3): 522-529 (1986).
Okuno, K., et al., "An Analysis of Target Preferences of *Escherichia coli* Outer-membrane Endoprotease OmpT for Use in Therapeutic Peptide Production: Efficient Cleavage of Substrates with Basic Amino Acids at the P4 and P6 Positions," *Biotechnology and Applied Biochemistry*, 36(2): 77-84 (2002).
Pütsep, K. et al., "Germ-free and Colonized Mice Generate the Same Products from Enteric Prodefensins," *J. Biol. Chem.* 275(51): 40478-40482, (2000).
Schmidtchen, A., et al., "Proteinases of common pathogenic bacteria degrade and inactivate the antibacterial peptide LL-37," *Molecular Microbiology*, 46(1): 157-168 (2002).
Sieprawska-Lupa, M., et al., "Degradation of human antimicrobial peptide LL-37 by *Staphylococcus aureus*-derived proteinases," *Antimicrobial Agents and Chemotherapy*, 48(12): 4673-4679 (2004).
Thong, W. and Benkovic, S.J. "Development of an Internally Quenched Fluorescent Substrate for *Escherichia coli* Leader Peptidase," Analytical Biochemistry, 255:66-73 (1998).

(Continued)

*Primary Examiner* — Nita M Minnifield
*Assistant Examiner* — Brian J Gangle
(74) *Attorney, Agent, or Firm* — Morgan, Lewis & Bockius LLP

(57) ABSTRACT

Described herein are methods of detecting a wound infection and for detecting the presence or absence of microorganisms, for example, wound pathogens in a sample, by contacting a sample with a cationic anti-microbial peptide that is degradable by an enzyme produced and/or secreted by a microorganism, and detecting degradation or the absence of degradation of the peptide, as an indicator of the presence or absence of the enzyme in the sample, and thus indicative of the presence or absence of a microorganism in the sample. The present invention also features a biosensor for detecting the presence or absence of a microorganism in a sample.

20 Claims, 4 Drawing Sheets

OTHER PUBLICATIONS

Yolken, Robert H., "Enzymic Analysis for Rapid Detection of Microbial Infection in Human Body Fluids: An Overview," *Clin. Chem.* 27(9): 1490-1498 (1981).

Fontana, C., et al., "Twelve Aberrant Strains of *Staphylococcus aureus* subsp. aureus from Clinical Specimens," *J. Clin. Micrbiol.*, 31(8): 2105-2109 (1993).

Gaillot, O., et al., "Evaluation of CHROMagar *Staph. aueus*, a New Chromogenic Medium, for Isolation and Presumptive Identification of *Staphylococcus aureus* from Human Clinical Specimens," *J. Clin. Microbial.*, 38(4): 1587-1591 (2000).

Perry, J.D., et al., "ABC Medium, a New Chromogenic Agar for Selective Isolation of *Salmonella* spp.,"*J. Clin. Microbial.*, 37(3): 766-768 (1999).

http://en.wikipedia.org/wiki/Oxidase_test.
http://en.wikipedia.org/wiki/Nitrate_reductase_test.
http://en.wikipedia.org/wiki/Indole_test.
http://en.wikipedia.org/wiki/GUS_reporter_system.
http://www.bact.wisc.edu/microtextbook/index.php?module=Book& func=displayarticle&art_id= I 19.

* cited by examiner

A     LLGDFFRKSKEKIGKEFKRIVQRIKDFLRNLVPRTES

B     LL1     (dabcyl-K)EKIGKEFKRIVQ(E-edans)

C     LL 2     (dabcyl-K)VQRIKDFLRNLV(E-edans)

FIG. 1A, 1B AND 1C

Schematic representation of LL-37 peptides used in the assay

Broad spectrum assay using LL 1 peptide.

Broad spectrum assay using LL 2 peptide

Assay using LL2 peptide in sterile wound fluid

```
                        SEQUENCE LISTING

<160> NUMBER OF SEQ ID NOS: 5

<210> SEQ ID NO 1
<211> LENGTH: 12
<212> TYPE: PRT
<213> ORGANISM: Artificial Sequence
<220> FEATURE:
<223> OTHER INFORMATION: Synthesized peptide

<400> SEQUENCE: 1

Glu Lys Ile Gly Lys Glu Phe Lys Arg Ile Val Gln
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Synthesized peptide

<400> SEQUENCE: 2

Val Gln Arg Ile Lys Asp Phe Leu Arg Asn Leu Val
1               5                   10

<210> SEQ ID NO 3
<211> LENGTH: 37
<212> TYPE: PRT
<213> ORGANISM: Artificial Sequence
<220> FEATURE:
<223> OTHER INFORMATION: Synthesized peptide

<400> SEQUENCE: 3

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
        35

<210> SEQ ID NO 4
<211> LENGTH: 14
<212> TYPE: PRT
<213> ORGANISM: Artificial Sequence
<220> FEATURE:
<223> OTHER INFORMATION: Synthesized peptide

<400> SEQUENCE: 4

Lys Glu Lys Ile Gly Lys Glu Phe Lys Arg Ile Val Gln Glu
```

```
<210> SEQ ID NO 5
<211> LENGTH: 14
<212> TYPE: PRT
<213> ORGANISM: Artificial Sequence
<220> FEATURE:
<223> OTHER INFORMATION: Synthesized peptide

<400> SEQUENCE: 5

Lys Val Gln Arg Ile Lys Asp Phe Leu Arg Asn Leu Val Glu
 1               5                  10
```

CATIONIC ANTI-MICROBIAL PEPTIDES AND METHODS OF USE THEREOF

RELATED APPLICATIONS

This application is the U.S. National Stage of International Application No. PCT/US2004/002636, filed 30 Jan. 2004, published in English, which claims the benefit of U.S. Provisional Application No. 60/444,521, filed 31 Jan. 2003. The entire teachings of the above applications are incorporated herein by reference.

BACKGROUND OF THE INVENTION

Infection of wounds is a major source of healthcare expenditure in the United States. Approximately 5% of all surgical wounds become infected with microorganisms, and that figure is considerably higher (10-20%) for patients undergoing abdominal surgery. Colonization rates are significantly higher in the hospital setting, both among healthcare workers, and among patients. Moreover, the colonizing organisms in the hospital environment are likely to be resistant to many forms of anti-microbial therapy, due to the strong selective pressure that exists in the nosocomial environment, where antibiotics are frequently used. For example, Staphylococci are usually carried as harmless commensals, however given a breach in the epidermis, they can cause severe, even life threatening infection in the human host.

Anti-microbial host defense peptides have been recognized as effector molecules of the innate immune system that are considered integral to the first line of defense to fight microbial infections. Such anti-microbial peptides are widely distributed among species. These peptides are characterized by cationic properties that facilitate interactions with the negatively charged phospholipids of the bacterial membrane. Anti-microbial peptides have been shown to kill by permeabilizing the membrane of microbial organisms. For example, it has been shown that defense peptide molecules can aggregate and form voltage dependent channels in the lipid bilayer resulting in the permeabilization of both the inner and outer membrane of the microorganism (Lehrer, R. I., *J. Clin. Investigation.*, 84:553 (1989)). The amphiphilic nature of these molecules facilitates the insertion of the hydrophobic residue into the lipid bilayer by electrostatic attraction while the polar residues project into and above the membrane.

Resistance to anti-microbial peptides is one of the key virulence factors of a successful pathogen. Pathogenic microorganisms have evolved several mechanisms by which they counteract the anti-microbial effect of these peptides. These include (i) covalent modifications of anionic molecules to reduce the negative charge of the bacterial cell envelope (ii) efflux of anti-microbial peptides via the proton-motive-force dependent efflux pumps (iii) alteration of the membrane fluidity and (iv) inactivation of anti-microbial peptides by proteolytic cleavage. These mechanisms of peptide resistance lead to the establishment of infection in the host.

The most common way of preventing microbial infection is to administer prophylactic antibiotic drugs. While generally effective, this strategy has the unintended effect of breeding resistant strains of bacteria. The routine use of prophylactic antibiotics should be discouraged for the very reason that it is encouraging the growth of resistant strains Rather than using routine prophylaxis, a better approach is to practice good wound management, i.e., keep the area free from bacteria before, during, and after surgery, and carefully monitor the wound site for infection during healing. Normal monitoring methods include close observation of the wound site for slow healing, signs of inflammation and pus, as well as measuring the patient's temperature for signs of fever. Unfortunately, many symptoms are only evident after the infection is already established. Furthermore, after a patient is discharged from the hospital they become responsible for monitoring their own healthcare, and the symptoms of infection may not be evident to the unskilled patient.

A system or biosensor that can detect the early stages of infection before symptoms develop would be advantageous to both patients and healthcare workers. If a patient can accurately monitor the condition of a wound after discharge, then appropriate anti-microbial therapy can be initiated early enough to prevent a more serious infection.

SUMMARY OF THE INVENTION

The present invention encompasses specific and broad spectrum detection assays, and biosensors for the detection of microorganisms, e.g., pathogenic bacteria, in a sample. Cationic Anti-Microbial Peptides (CAMPs) are molecules that are degraded, or cleaved, by molecules e.g., enzymes such as proteinases, that are secreted by microorganisms, such as bacteria or fungi, or expressed on the cell surface of microorganisms. The degradation or cleavage of one, or more CAMPs, (which leads to the inactivation of the CAMP) as described herein, can serve as a marker for the detection of the presence or absence of a microorganism in a sample, for example, a wound or body fluid. Accordingly, the present invention features a method of detecting the presence or absence of one, or more, microorganisms in a sample by detecting the presence or absence of the degradation of one or more CAMPs by an enzyme, e.g., a proteinase, present in the sample. In one aspect, the invention features a method for detecting the presence or absence of one, or more, microorganisms in a biological sample, comprising the steps of contacting the sample with a detectably labeled cationic anti-microbial peptide that is modified (e.g., structurally altered) such as by cleavage, also referred to herein as a degradable peptide by an enzyme produced and/or secreted by the microorganism, under conditions that result in modification of the CAMP by the enzyme; and detecting the modification or the absence of the modification of the CAMP. As used herein, the term modification means degradation or cleavage, wherein the CAMP is degraded (e.g., inactivated) from an intact peptide of a characteristic length (e.g., defined by a certain number of amino acid residues for that CAMP), into two or more, smaller amino acid fragments. The degradation of the CAMP into smaller fragments results in a detectable signal. Modification of the CAMP, and detection of the signal, indicates the presence of one, or more, microorganism in the sample, and the absence of degradation of the CAMP (no detectable signal produced) indicates the absence of the microorganism in the sample and/or the absence of the enzyme that is specific for cleaving the peptide. The enzymes of the present invention are typically proteinases, proteases, elastases, gelatinases and other enzymes implicated in proteolytic degradation of CAMPs.

It should be noted that a number of different organisms can inactivate (degrade) the same, or substantially similar, CAMP. Thus, in a particular aspect of this invention, a broad spectrum assay is contemplated wherein multiple microorganisms can be detected by the degradation of only one CAMP. Alternatively, a consensus amino acid sequence can be determined that simulates the sequence of two or more CAMPs and thus acts as a substrate for more than one microorganism.

In another aspect, the present invention features a method for diagnosing the presence or absence of a wound infection in a subject, comprising the steps of a) contacting a sample obtained from a wound in a subject with one, or more, detectably labeled CAMPs that are capable of being degraded (degradable) by an enzyme produced and/or secreted by a microorganism, under conditions that result in modification of the CAMP by the enzyme; and b) detecting a modification or the absence of a modification of the CAMP. Modification of the CAMP indicates the presence of a wound infection in the subject, and the absence of modification of the CAMP indicates the absence of an infection in the subject.

In another aspect, the invention features a biosensor for detecting the presence or absence of a microorganism in a sample, comprising a solid support and one, or more, detectably labeled CAMPs that are degradable by an enzyme produced and/or secreted by the microorganism, wherein the CAMP is attached to the solid support. Attachment can be accomplished by any number of ways known to those of skill in the art for attaching peptides to solid supports. Importantly, the attachment must still render the peptide in a conformation that is suitable for detection, i.e., that a detectable signal is generated upon degradation.

In still another aspect, the present invention features a kit for detecting a wound infection comprising a biosensor for detecting the presence or absence of a microorganism in a sample, and one or more reagents for detecting the presence of the microorganism that is the causative agent of the wound infection. For example, the reagent can be used to detect an enzyme secreted by the microorganism. In particular, the reagent can be used to detect the modification of the CAMP of the biosensor.

CAMPs (cationic anti-microbial peptides) are normally present in a wound and the presence of pathogenic microorganisms capable of degrading these peptides can therefore be used as a marker for infection.

BRIEF DESCRIPTION OF THE DRAWINGS

FIG. 1A shows the relative positions of the cleavage points in the LL-37 peptide (SEQ ID NO. 3). The putative antibacterial region of LL-37 is underlined (from Schmidtchen A et al., 2002).

FIGS. 1B and 1C show the amino acid sequence of the peptide substrates, LL 1 and LL 2 (SEQ ID NOS. 4-5) used in the assays.

DETAILED DESCRIPTION OF THE INVENTION

Figure 2:
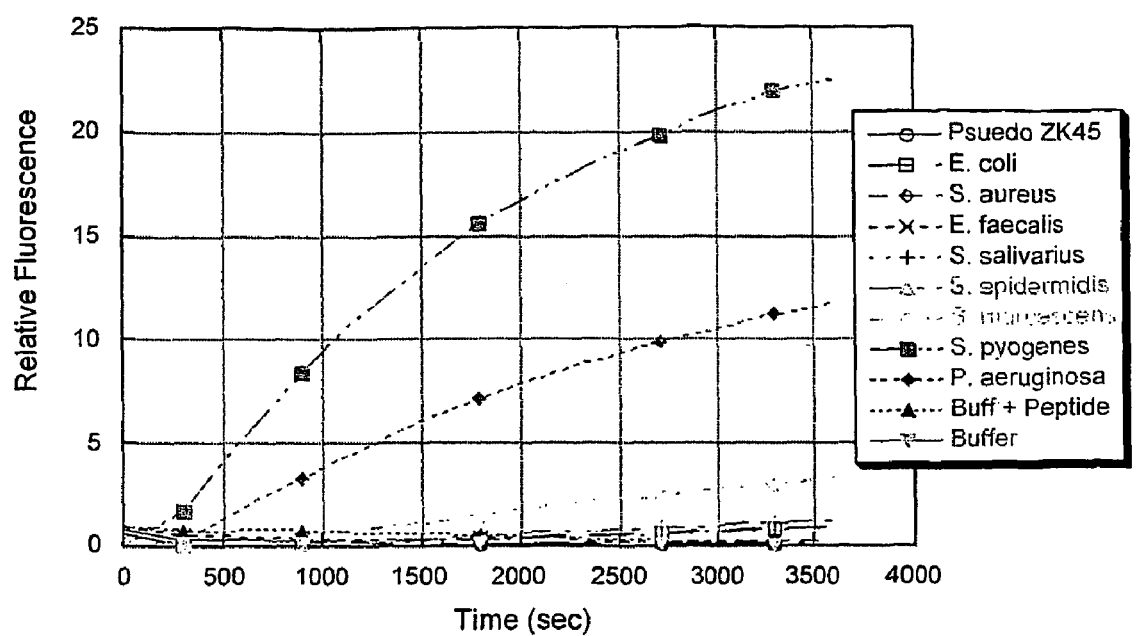
FIG. 2 is a graph showing the results of an assay using the peptide LL 1.

In humans, three types of anti-microbial peptides have been identified. These peptides are referred to herein as Cationic Anti-Microbial Peptides, or CAMPs.

Defensins or "Endogenous Antibiotics".

Defensins are the largest and best studied class of anti-microbial peptides secreted by mammalian cells (neutrophils, intestinal Paneth cells, and barrier epithelial cells). They counter microbial, fungal. as well as viral infection (Cole, A. M., et al., *Biotechniques*, 4:822 (2000)) and thus serve as a first line of defense against the invading pathogens. In addition to the role of defensins in host defense, they are thought to play a role in inflammatory disorders, wound repair, and the promotion of adaptive immune responses (Wetering V. S., et al., *J. Allergy Clin. Immunol.* 104:1131-1138 (1994)). These cationic proteins/polypeptides are arginine rich and possess six cysteine residues that form three intramolecular disulfide bridges, a hallmark feature of defensins (Tang, Y. Q., et al., *Science* 286:498-502 (1999) and Lenova, L., et al., *Proct. Natl. Acad. Sci.*, 99:1813 (2001)). Based on spacing of the cysteine residues and alignment of disulphide bridges, three groups of mammalian defensins have been identified to date, which include (i) α (human neutrophil peptide, HNP), (ii) β (human beta-defensins, hBD-2) and (iii) θ (circular, or 'theta" minidefensin) subfamily (Tang, Y. Q., et al., *Science* 286:498-502 (1999)). The role of defensins as a potential therapeutic agent has been substantiated by recent findings of Tang et al., who have shown direct involvement of α-defensins in slowing the progression of HIV infection in infected individuals. Defensins also play an important role in fighting *E. coli* infections.

Cathelicidins

Cathelicidins are a class of anti-microbial peptides encoded exclusively by mammals. They are bipartite molecules with an N-terminal cathelin domain and a C-terminal antimicrobial domain (LL-37). In humans, cathelicidin is encoded by the hCAP-18 gene. The serine protease, proteinase 3, facilitates the cleavage of the active peptide LL-37 (antimicrobial domain of hCAP-18), which then exerts antibacterial activity against both Gram-positive and Gram-negative bacteria (Sorensen, O. E., et al., *Blood*, 97:3951-3959 (2001)). More recent studies have shown that LL-37 may act in synergy with the well-characterized antimicrobial peptide, α-defensin, to clear bacterial infections. In addition to host defense, this class of gene-encoded antibiotics are involved in additional functions which include chemotactic activity, mitogenesis, and angiogenesis (Lehrer, R. I., et al., *Curr. Opin. Immunol.*, 14:96 (2002) and Lehrer, R. I., et al., *Curr. Opin. Hematol.*, 9: 18-22 (2002)). Due to the involvement of these peptides in diverse functions, they are also termed as "multifunctional effector molecules."

Thrombocidins (Thrombocyte Microbicidal Proteins)

Thrombocidins are truncated versions (carboxy terminal deletions) of the CXC chemokines which are released upon the activation of the blood platelets, hence the name thromobocidins (Zaat et al. 1994). They have been previously demonstrated to clear Streptococcal, Staphylococcal and *Candida* infections in in vitro experimental models (Dankert, J., et al., *Infect. Immun.*, 63:663-671 (1995)).

Degradation of CAMPs by proteinases of pathogenic bacteria is fairly well characterized. It has been demonstrated previously that pathogenic bacteria secrete proteinases such as elastases, cysteine proteases, and alkaline proteinases, which modify host responses like kallikreins, coagulation factors, complement, cytokines, and antiproteinases (Travis, J., *Trends Microbiol.*, 3:405-407 (1995)). Interestingly, analyses of wound fluids revealed an abundance of degradation product of the above mentioned host factors. These results suggest a direct role of proteinases in modulation of the host factors, leading to enhanced survival and proliferation of the pathogen. The fact that proteinases play a major role in virulence of the microorganism, has been further substantiated by recent in vitro findings that proteinases secreted by *Pseudomonas aeruginosa, Enterococcus faecalis, Proteus mirabilis*, and *Streptococcus pyogenes* degrade antibacterial peptides, especially, LL-37 (Schmidtchen, A., et al., *Mol. Microbiol.*, 46:157-168 (2002)). Further, wound fluid from a chronic ulcer of a *P. aeruginosa* infected patient resulted in complete degradation of LL-37, while fluid from a sterile wound did not show this effect (Schmidtchen, A., et al., *Mol. Microbiol.*, 46:157-168 (2002)).

Armed with the knowledge of the cleavage points of different proteinases on the LL-37 (FIG. 1A), together with the understanding that a number of human pathogens can cleave this antibacterial peptide, two variants of LL-37 (FIGS. 1B and C) have been generated and have been used these as candidate substrates for a bacterial detection assay (e.g. for *S. pyogenes*).

The enzymes of the present invention can modify substrates, for example, proteins or polypeptides (e.g., CAMPs) by cleavage, and such modification can be detected to determine the presence or absence of a pathogen in a sample. One method for detecting modification of a substrate by an enzyme is to label the substrate with two different dyes, where one serves to quench fluorescence of the other (fluorescence resonance energy transfer or FRET) when the molecules, for example, dyes or calorimetric substances are in close proximity, and is measured by fluorescence.

FRET is the process of a distance dependent excited state interaction in which the emission of one fluorescent molecule is coupled to the excitation of another. A typical acceptor and donor pair for resonance energy transfer consists of 4-[[-(dimethylamino)phenyl]azo]benzoic acid (DABCYL) and 5-[(2-aminoethylamino)naphthalene sulfonic acid (EDANS). EDANS is excited by illumination with 336 nm light, and emits a photon with wavelength 490 nm. If a DABCYL moiety is located within 20 angstroms of the EDANS, this photon will be efficiently absorbed. DABCYL and EDANS will be attached to opposite ends of a peptide substrate. If the substrate is intact, FRET will be very efficient. If the peptide has been cleaved by an enzyme, the two dyes will no longer be in close proximity and FRET will be inefficient. The cleavage reaction can be followed by observing either a decrease in DABCYL fluorescence or an increase in EDANS fluorescence (loss of quenching).

If the substrate to be modified is a protein, peptide, or polypeptide, the substrate can be produced using standard recombinant protein techniques (see for example, Ausubel et al., "Current Protocols in Molecular Biology," John Wiley & Sons, (1998), the entire teachings of which are incorporated by reference herein). In addition, the enzyme of the present invention can also be generated using recombinant or synthetic techniques. Through an ample supply of enzymes or its substrate, the exact site of modification can be determined, and a more specific substrate of the enzyme can be defined, if so desired. This substrate can also be used to assay for the presence of the pathogenic bacteria.

The substrates are labeled with a detectable label that is used to monitor interactions between the enzyme and the substrate and detect any substrate modifications, for example, cleavage of the substrate or label resulting from such interactions. Examples of detectable labels include various dyes that can be incorporated into substrates, for example, those described herein, spin labels, antigen or epitope tags, haptens, enzyme labels, prosthetic groups, fluorescent materials, chemiluminescent materials, bioluminescent materials, and radioactive materials. Examples of suitable enzyme labels include horseradish peroxidase, alkaline phosphatase, .beta.-galactosidase, and acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride and phycoerythrin; an example of a chemiluminescent material includes luminol; examples of bioluminescent materials include luciferase, luciferin, and acquorin, and examples of suitable radioactive material include $^{125}I$, $^{131}I$, $^{35}S$, and $^3H$. Other examples of detectable labels include BODIPY, Pyrene, Texas Red, EDANS, Dansyl Aziridine, IATR and fluorescein. Succimidyl esters, isothiocyanates, and iodoacetamides of these labels are also commercially available. When detectable labels are not employed, enzymatic activity can be determined by other suitable methods, for example detection of substrate cleavage through electrophoretic analysis, or other methods known to one skilled in the art.

One example of a detectable label is a chromogenic dye that allows monitoring of the hydrolysis of the substrate by the bacterial enzyme. An example of such a dye is para-nitrophenol. When conjugated to a substrate molecule, this dye will remain colorless until the substrate is modified by the secreted enzyme, at which point it turns yellow. The progress of the enzyme-substrate interaction can be monitored by measuring absorbance at 415 nm in a spectrophotometer. Other dyes that produce detectable modification, e.g., a visible color change, are known to those of skill in the art.

The sample in which the presence or absence of bacteria is detected, or a wound infection is diagnosed, can be, for example, a wound, a body fluid such as blood, urine, sputum, or wound fluid (for example, pus produced at a wound site). The sample can also be any article that bacteria may be contained on/in, for example, a catheter, a urine collection bag, a blood collection bag, a plasma collection bag, a disk, a scope, a filter, a lens, foam, cloth, paper, a suture, swab, wound dressing, test tube, a well of a microplate, contact lens, any suitable polymer or a swab from an area of a room or building, for example, an examination room or operating room of a healthcare facility, a bathroom, a kitchen, or a process or manufacturing facility.

The present invention also features a biosensor for detecting one or more microorganisms by their degradation of one or more, CAMPs as described herein, and for notifying a consumer of the presence of the microorganism. A biosensor for use in healthcare settings or home-use to detect infected wounds comprising a (one or more) CAMP(s) that is attached to a solid support that is proximal to a wound or other body fluid that is being monitored for bacterial contamination is provided. Preferably, the CAMP is covalently bound to a label and thus has a detection signal that upon degradation of the substrate-label or an internal substrate bond indicates the presence of the microorganism.

The biosensor is made by first determining the CAMP to be degraded by a specific enzyme characteristic of the microorganism(s) to be detected. The determined CAMP is labeled with one or more, and preferably, a plurality of detectable labels, for example, chromatogenic or fluorescent leaving groups. For example, the labeling group provides a latent signal that is activated only when the signal is proteolytically detached from the substrate or is hydrolyzed in the middle of the substrate. Chromatogenic leaving groups include, for example, para-nitroanalide groups. Should the CAMP come into contact with an enzyme secreted into a wound or other body fluid by bacteria or presented on the surface of a bacterial cell, the enzyme modifies the substrates in a manner that results in detection of such a modification, for example, a change in absorbance, which can be detected visually as a change in color (for example, on the solid support, such as a wound dressing), or using spectrophotometric techniques standard in the art.

The biosensor is a solid support, for example, a wound dressing (such as a bandage, or gauze), any material that needs to be sterile or free of microbial contamination, for example, a disk, scope, filter, lens, foam, cloth, paper, or sutures, or an article that contains or collects the sample (such as a urine collection bag, blood or plasma collection bag, test tube, catheter, swab, or well of a microplate).

Typically, the solid support is made from materials suitable for sterilization if the support directly contacts the wound or sample. In one embodiment of the present invention, the biosensor can be directly contacted with the wound. In some instances, a sterile covering or layer is used to prevent contamination of the wound or body fluid upon such direct contact. If such sterile coverings are used, they will have properties that make them suitable for sterilization, yet do not interfere with the enzyme/substrate interaction. Preferably, the portion of the biosensor that comes into contact with the wound is also nonadherent to permit easy removal of the biosensor from the sample surface. For example, if the biosensor comprises a wound dressing, the dressing contacts the wound for a time sufficient for the enzyme substrate to react and then the dressing is removed from the wound without causing further damage to the wound or surrounding tissue.

CAMPs suitably labeled with detectable labels, for example, a chromogenic dye, and attached or incorporated into a sensor apparatus, can act as indicators of the presence or absence of pathogenic bacteria that secrete the aforementioned enzymes. When more than one CAMP is utilized, each may be labeled so as to distinguish it from another (for example, using different detectable labels) and/or each may be localized in a particular region on the solid support.

CAMPs with hydrophobic leaving groups can be non-covalently bound to hydrophobic surfaces. Alternatively hydrophilic or hydrophobic substrates can be coupled to surfaces by disulfide or primary amine, carboxyl or hydroxyl groups. Methods for coupling substrates to a solid support are known in the art. For example, fluorescent and chromogenic substrates can be coupled to solid substrates using non-essential reactive termini such as free amines, carboxylic acids or SH groups that do not effect the reaction with the wound pathogens. Free amines can be coupled to carboxyl groups on the substrate using, for example, a 10 fold molar excess of either N-ethyl-N'-(3-dimethylaminopropyl)carbodiimide hydrochloride (EDC) or N-cyclohexyl-N'-2-(4'-methyl-morpholinium)ethyl carbodiimide-p-toluene sulphonate (CMC) for 2 hrs at 4° C. in distilled water adjusted to pH 4.5 to stimulate the condensation reaction to form a peptide linkage. SH groups can be reduced with DTT or TCEP and then coupled to a free amino group on a surface with N-e-Male-imidocaproic acid (Griffith, et al., *Febs Lett.*, 134:261-263 (1981)).

Examples of CAMPs for use in the present invention are polypeptides comprising or essentially consisting of the amino acid sequence of SEQ ID NO: 1 EKIGKEFKRIVQ; SEQ ID NO: 2 VQRIKDFLRNLV, and SEQ ID NO: 3 LLGDFFRKSKEKIGKE FKRIVQRIKDFLRNLVPRTES or a polypeptide having at least 50%, 60%, 70%, 80%, 85%, 90%, 95%, or 99% sequence identity to SEQ ID NOS. 1-3, as determined using a sequence comparison program and parameters known to those of skill in the art.

The polypeptides of the present invention also encompass fragments and sequence variants of the polypeptides described above, and also variants of SEQ ID NOS: 1, 2 or 3. Variants include a substantially homologous polypeptide encoded by the same genetic locus in an organism, i.e., an allelic variant, as well as other variants. Variants also encompass polypeptides derived from other genetic loci in an organism, but having substantial homology to a polypeptide of SEQ ID NOS: 1, 2 or 3. Variants also include polypeptides substantially homologous or identical to these polypeptides but derived from another organism, i.e., an ortholog. Variants also include polypeptides that are substantially homologous or identical to these polypeptides that are produced by chemical synthesis. Variants also include polypeptides that are substantially homologous or identical to these polypeptides that are produced by recombinant methods.

The percent identity of two amino acid sequences can be determined by aligning the sequences for optimal comparison purposes (e.g., gaps can be introduced in the sequence of a first sequence). The amino acids at corresponding positions are then compared, and the percent identity between the two sequences is a function of the number of identical positions shared by the sequences (i.e., % identity=# of identical positions/total # of positions×100). In certain embodiments, the length of the amino acid sequence aligned for comparison purposes is at least 30%, preferably, at least 40%, more preferably, at least 60%, and even more preferably, at least 70%, 80%, 90%, or 100% of the length of the reference sequence. The actual comparison of the two sequences can be accomplished by well-known methods, for example, using a mathematical algorithm. A preferred, non-limiting example of such a mathematical algorithm is described in Karlin, et al., *Proc. Natl. Acad. Sci. USA*, 90:5873-5877 (1993). Such an algorithm is incorporated into the BLAST programs (version 2.2) as described in Schaffer, et al., *Nucleic Acids Res.*, 29:2994-3005 (2001). When utilizing BLAST and Gapped BLAST programs, the default parameters of the respective programs can be used. In one embodiment, the database searched is a non-redundant (NR) database, and parameters for sequence comparison can be set at: no filters; Expect value of 10; Word Size of 3; the Matrix is BLOSUM62; and Gap Costs have an Existence of 11 and an Extension of 1.

In another embodiment, the percent identity between two amino acid sequences can be accomplished using the GAP program in the GCG software package (available on the worldwide web at the website accelrys.com, as available on Aug. 31, 2001) using either a Blossom 63 matrix or a PAM250 matrix, and a gap weight of 12, 10, 8, 6, or 4 and a length weight of 2, 3, or 4. In yet another embodiment, the percent identity between two nucleic acid sequences can be accomplished using the GAP program in the GCG software package (available on the worldwide web at the website cgc.com), using a gap weight of 50 and a length weight of 3.

The invention also encompasses polypeptides having a lower degree of identity but having sufficient similarity so as to perform one or more of the same functions performed by an polypeptide encoded by a nucleic acid molecule of the invention, e.g., the ability to act as a CAMP. Similarity is determined by conserved amino acid substitution. Such substitutions are those that substitute a given amino acid in a polypeptide by another amino acid of like characteristics. Conservative substitutions are likely to be phenotypically silent. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gin; exchange of the basic residues Lys and Arg; and replacements among the aromatic residues Phe and Tyr. Guidance concerning which amino acid changes are likely to be phenotypically silent are found in Bowie, et al., *Science*, 247:1306-1310 (1990).

Functional variants can also contain substitution of similar amino acids that result in no change or an insignificant change in function. Alternatively, such substitutions may positively or negatively affect function to some degree. Non-functional variants typically contain one or more non-conservative amino acid substitutions, deletions, insertions, inversions, or truncation or a substitution, insertion, inversion, or deletion in a critical residue or critical region, such critical regions include the cleavage site for a CAMP.

Amino acids in a polypeptide of the present invention that are essential for cleavage by an enzyme, and thus degradation, can be identified by methods known in the art, such as site-directed mutagenesis or alanine-scanning mutagenesis (Cunningham, et al., *Science*, 244:1081-1085 (1989)). The latter procedure introduces a single alanine mutation at each of the residues in the molecule (one mutation per molecule).

The invention also includes polypeptide fragments of the amino acid sequence of SEQ ID NOS: 1, 2 or 3, or functional variants thereof. Fragments can be derived from a polypeptide comprising SEQ ID NOS: 1, 2. or 3 wherein those fragments contain at least one enzymatic reaction site (e.g. a site of enzymatic cleavage by a proteinase). The present invention also encompasses fragments of the variants of the polypeptides described herein. Useful fragments include those that retain the ability to act as substrates for an enzyme capable of degrading a CAMP as described herein. Fragments can be discrete (not fused to other amino acids or polypeptides) or can be within a larger polypeptide. Further, several fragments can be comprised within a single larger polypeptide. In one embodiment a fragment designed for expression in a host can have heterologous pre- and pro-polypeptide regions fused to the amino terminus of the polypeptide fragment and an additional region fused to the carboxyl terminus of the fragment.

The biosensors of the present invention can be used in any situation where it is desirable to detect the presence or absence of microorganisms, and in particular, pathogenic bacteria, viruses and fungi. For example, bacteria that collects on work surfaces in health care facilities, and in particular in operating rooms can be detected with a biosensor as described herein. A CAMP, or more than one CAMP, that can be modified by an enzyme secreted by or presented on the surface of a bacteria is labeled and covalently bound to a collector substrate, such as cotton fibers on the tip of a swab. When more than one CAMP is utilized, each may be labeled so as to distinguish it from another (for example, using different detectable labels) and/or each may be localized in a particular region on the solid support. The swab tip is used to wipe the surface suspected of being contaminated by bacteria. The swab tip is placed in a medium and incubated using conditions that allow modification of the labeled CAMP if an enzyme specific for the bound, labeled CAMP(s) is present.

The present invention also features a kit for detecting wound-specific bacteria as described herein. The kit can comprise a solid support, for example, having a plurality of wells (e.g., a microtiter plate), to which a detectably labeled CAMP is linked, coupled, or attached. A means for providing one or more buffer solutions is provided. A negative control and/or a positive control can also be provided. Suitable controls can easily be derived by one of skill in the art. A sample suspected of being contaminated by a pathogen described herein is prepared using the buffer solution(s). An aliquot of the sample, negative control, and positive control is placed in its own well and allowed to react. Those wells where modification of the substrate, for example, a color change is observed are determined to contain a microbial pathogen. Such a kit is particularly useful for detecting a wound infection in a subject.

Also encompassed by the present invention is a kit that comprises a biosensor, such as a packaged sterilized wound dressing, and any additional reagents necessary to perform the detection assay.

A method for developing an assay for detecting a pathogenic microorganism that produces at least one enzyme that is secreted by the cell or present on the surface of the cell and is capable of degrading CAMPs, and a method for using the assay to detect microorganisms producing the enzyme(s) now follows:

Step 1) Define an amino acid sequence that uniquely identifies the prokaryotic microorganism of interest. Alternatively, an (one or more) amino acid sequence that is unique to a specific group of pathogens, for example, wound-specific pathogens can be determined.

Select an amino acid sequence, for example, a protein, peptide, or polypeptide (marker sequence) that uniquely characterizes or marks the presence of the microorganism or group of microorganisms (for example, wound-specific pathogens) of interest. The selection can be performed utilizing a bioinfomatic approach, for example, as described in detail below. One or more amino acid sequences that are unique to a specific prokaryotic microorganism are determined.

Step 2) Obtain sufficient enzyme to determine conditions facilitating optimal modification of a substrate by the enzyme.

Isolate the enzyme from the extracellular medium in which the pathogenic bacteria to be assayed is growing, or from the cell membrane of the bacteria, using standard protein purification techniques, described, for example, in Ausubel (supra).

Alternatively, if the genetic sequence encoding the enzyme or the location of the genetic sequence encoding the enzyme are unknown, isolate and clone the genetic sequence encoding the marker amino acid of Step 1, or, first determine the genetic sequence, and then proceed as before.

Step 3) Determine the conditions for growth of the prokaryotic organism and for the production of an enzyme presented on the surface of the cell or secreted by the cell.

Determine medium required for growth of the specific prokaryotic microorganism of interest and for expression of its unique active enzyme into the medium. Also determine whether a second molecule, for example, an enzyme is required to convert the specific enzyme from an inactive precursor form to an active form. To determine if the enzyme has been secreted in an active form, a sample of the bacterial culture is provided with chosen potential substrates and cleavage of these substrates is determined. This can be done, for example, by combining the bacteria that produce the enzyme with the substrate in the appropriate media and incubating at 37° C. with gentle shaking. At preset times (0.1, 0.3, 1.0, 3.0, 5.0, 24 and 48 hours) the samples are centrifuged to spin down the bacteria, and a small aliquot is removed for a SDS-PAGE gel sample. After completion of the time course the samples are run on a 10-15% gradient SDS-PAGE mini-gel. Then, the proteins are transferred to Immobilon Pseq (Transfer buffer, 10% CAPS, 10% methanol pH 11.0, 15 V for 30 minutes) using a Bio-Rad semi-day transblotting apparatus. Following transfer of the proteins, the blot is stained with Coomassie blue R-250 (0.25% Coomassie Brilliant Blue R-250, 50% methanol, 10% acetic acid) and destained (high destain for 5 minutes, 50% methanol, 10% acetic acid; low destain until complete, 10% methanol, 10% acetic acid) followed by sequencing from the N-terminal. Alternatively, the samples will be run on a mass spectrometer in order to map the sites of proteolytic cleavage using a Voyager Elite Mass spectrometer (Perceptive Biosystems).

Step 4) Identify any specific cationic anti-microbial peptide substrate(s) of the active enzyme. Label each substrate with a detectable label, for example, a detectable label described herein, or any other detectable label known in the art.

Step 5) Increase the specificity of the enzyme-substrate interaction (optional) by determining the active or binding site of the enzyme (for example, using FRET as described above), then determining the genetic sequence useful for producing the active or binding site, and cloning the determined genetic sequence to generate a more specific substrate.

Step 6) Provide a biosensor comprising one or more of the detectably labeled substrates identified above for detection of the protease of the pathogenic bacteria of interest.

The substrate can be attached to solid support, for example, a wound dressing, or an article that holds the enzyme and substrate, for example, a body fluid collection tube or bag, a microplate well, or a test tube. The solid support, if desired, can provide a plurality of derivatized binding sites for coupling to the substrate, for example, succimidyl ester labeled primary amine sites on derivatized plates (Xenobind plates, Xenopore).

Optionally, unoccupied reactive sites on the solid support are blocked by coupling bovine serum albumin, or the active domain of p26 thereto. p26 is an alpha-crystallin type protein that is used in this case to reduce non specific protein aggregation. The ability of the p26 protein to refold heat denatured citrate synthetase before and after coupling to the surface of the food packaging is used as a control for determining p26 activity. Alpha-crystallin type proteins were recombinantly produced using standard recombinant DNA technologies (see Ausubel, supra). Briefly, the plasmid containing the beta sheet-charged core domain of p26 is electroporated into electrocompetent BL21(DE3) cells (BIO-RAD *E. coli* pulser). The cells are grown up to an OD of 0.8, then induced with 1 mM IPTG for 4 hours. The cells are spun down, and sonicated in low buffer (10 mM Tris, pH 8.0, 500 mM NaCl, 50 mM Imidizole) to lyse (Virsonic, Virtis, Gardiner, N.Y.). The lysate is spun down at 13,000.times.g for 10 minutes, and the supernatant 0.45 and 0.2 μm filtered. This filtrate is loaded onto a Ni-NTA superose column (Qiagen, Valencia, Calif., cat #30410). High buffer (10 mM Tris pH 8.0, 500 mM NaCl, 250 mM Imidizole) is used to elute the protein.

Allow the enzyme(s) to come into contact with the substrate(s), and monitor the reaction for a modification in the detectably labeled substrate, as described herein. Modification of the substrate indicates that the enzyme produced/secreted by the bacteria is present in the reaction. In addition, the absence of modification of the substrate indicates that the enzyme is not present in the sample. If the bacteria or enzyme is from a wound, modification of the substrate indicates that the bacteria is present in the wound, and that the wound is infected, while the absence of modification of the substrate indicates that the particular bacteria is not present in the wound, and that the wound is not infected with that particular bacteria.

EXAMPLES

The present invention will now be illustrated by the following Examples, which are not intended to be limiting in any way.

Example 1

Detection Assays

Two peptide substrates, LL 1 and LL 2, were synthesized so as to encompass all the cleavage sites of the LL-37 as shown in FIGS. 1A, 1B & C. The peptide substrates used here were labeled with the fluorescent probe edans (5-((2-amino-ethyl)amino)naphthalene-1-sulphonice acid) and the quencher dye molecule dabcyl((4-(4-(dimethylamino)phenyl)azo)benzoic acid).

The bacteria were grown in an incubator overnight at 37 C in 5 ml BHI (Brain Heart Infusion) media. Each of the resulting cultures was split into two samples. One was used as is, and the other was spun down and the supernatant was collected. The assays were run in 20 mM tris buffer (pH 7.4) with 150 mM NaCl added. The reaction was carried out with 7 ul of culture or supernatant and 3 ul peptide substrate (5 mg/ml in water) in 100 ul total volume at 37 C. The reaction was followed on a fluorimetric plate reader using an excitation wavelength of 355 nm and an emission wavelength of 485 nm.

The first set of experiments was performed by addition of the bacterial culture (media and cells) directly into the assay solution. If the protease is attached to the cell membrane it would not be expected to be found secreted into the media. Thus, the presence of cells would be necessary. The assay used peptide LL1 as the substrate and the results are shown in FIG. 2.

Bacterial cells used in this assay were grown to stationary phase in Brain Heart Infusion (BHI) medium. Briefly, 7.mu.l of bacterial culture was incubated with 3 μl of LL1 peptide substrate and 92 μl of phosphate buffered saline, pH 7.2). The reaction was followed on a 96 well microtiter plate reader using an excitation an emission wavelength of 355 nm and 538 nm respectively at 37° C. The reaction was monitored for a period of 1 hr. and plotted using the KALEIDAGRAPH software. Buffer, 20 mM Tris buffer (pH 7.4) with 150 mM NaCl. There was no cross-reactivity with *Pseudomonas*.

Some protease activity was observed for both *S. pyogenes* and *Pseudomonas* with this peptide. In addition, a small amount of activity was also observed for Serratia. The reaction was repeated with bacterial supernatant and the results were similar for *S. pyogenes*, but the reaction with *Pseudomonas* was reduced upon removal of the cells from the assay.

The assay was repeated using identical conditions with the peptide LL2.

Bacterial cells used in this assay were grown to stationary phase in Brain Heart Infusion (BHI) medium. The assay was performed as previously described.

Figure 3:
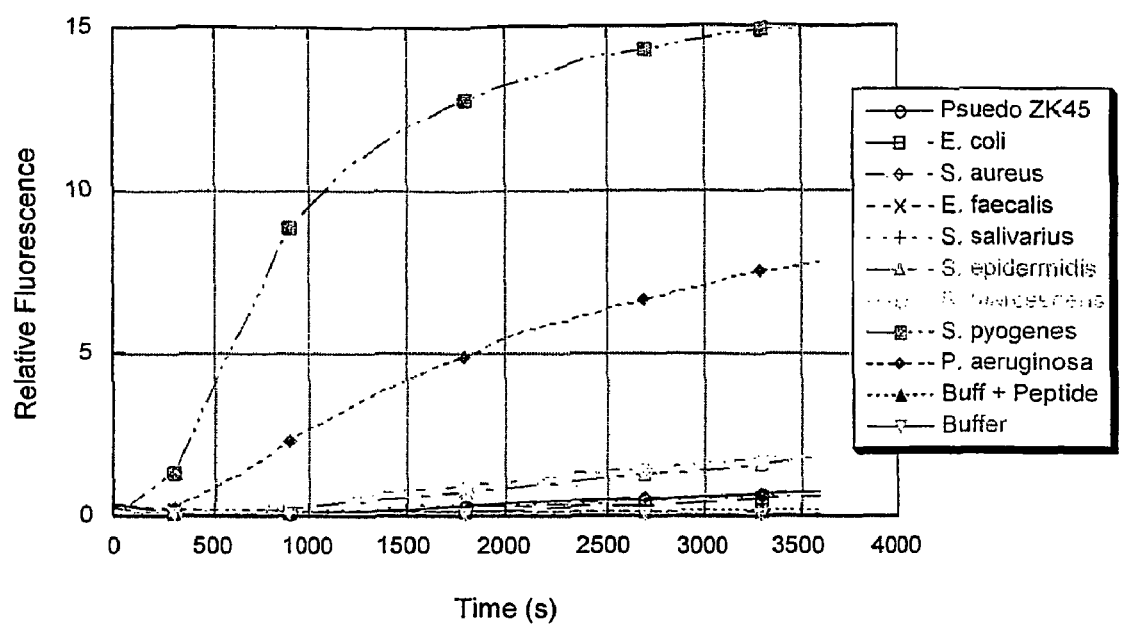
FIG. 3 is a graph showing the results of an assay using the peptide LL 2, which appears to be specific for S. pyogenes.

The results obtained with LL2 (shown in FIG. 3) were similar to the results obtained with LL1, except that the overall reactivity appears to be reduced somewhat. The assays run with cells and supernatant gave a similar curve for *S. pyogenes*, however, the activity for *Pseudomonas* was reduced upon removal of the cells from the assay.

Example 2

Porcine Wound Fluid Assay

In order to test for cross reactivity in a wound, the assays were performed under physiologically relevant conditions. The assay for LL1 and LL2 were tested using porcine wound fluid extract in place of reaction buffer.

Immediately after surgery to create partial thickness wounds for the sensor study a gauze dressing was placed on the wound. After a time the dressing was removed, bagged, and placed in a freezer at −80 C. Absorbed wound fluid was recovered from the dressing by incubation in 10 mls buffer (0.1M Tris-HCl, pH 7.4 with 0.1% TRITON X-100® non-ionic surfactant (Octylphenol ethylene oxide condensate; Sigma Aldrich, St. Louis, Mo.). The dressing was incubated on both sides for 2 hours at room temperature and squeezed out. The fluid obtained was aliquoted out and frozen at −20 C.

The bacteria were grown in an incubator overnight at 37 C in 5 ml BHI (Brain Heart Infusion) media. Each of the resulting cultures was spun down and the supernatant was collected. The assays were run in freshly thawed wound fluid. The reaction was carried out with 7 ul of culture or supernatant and 3 ul peptide substrate (5 mg/ml in water) in 100 ul total volume at 37 C. The reaction was followed on a fluorimetric plate reader using an excitation wavelength of 355 nm and an emission wavelength of 485 nm.

Figure 4:
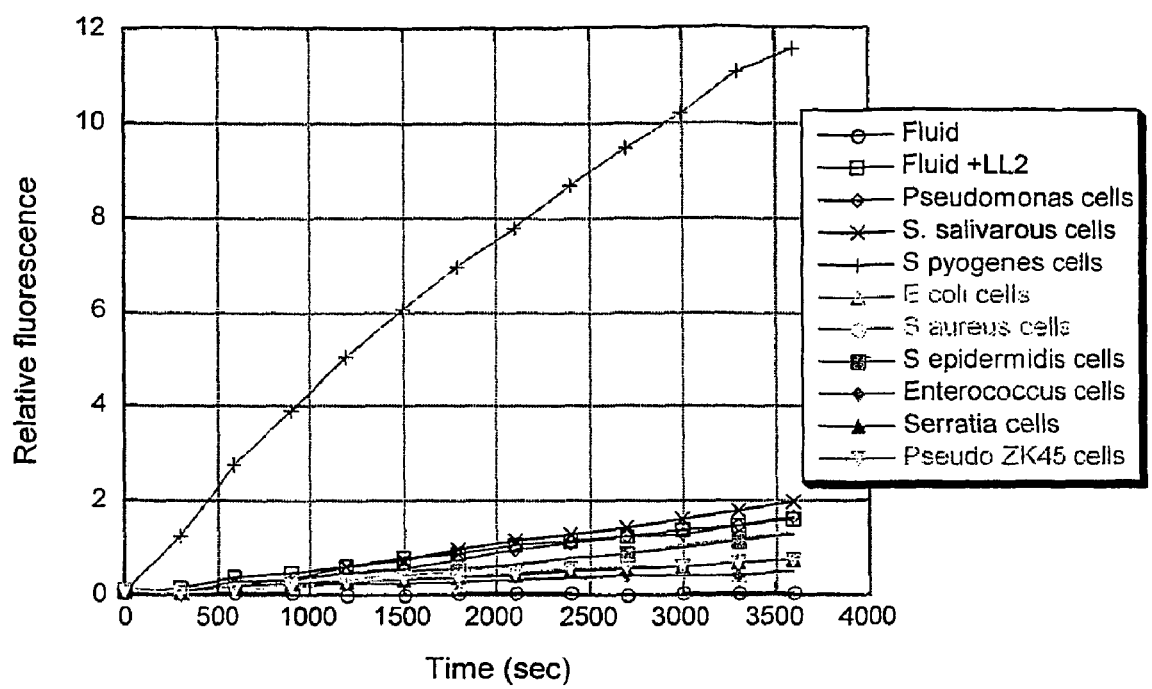
FIG. 4 is a graph showing the results of an assay using peptide LL 2 in wound fluid.

The protease assay was run using the LL2 peptide previously identified as a substrate for *S. pyogenes* and *Pseudomonas*. The results are shown in FIG. 4.

Bacterial cells used in this assay were grown to stationary phase in Brain Heart Infusion (PHI) medium. Briefly, 5 μl of bacterial culture was incubated with 3 μl of LL2 peptide substrate and 92 μl of sterile wound fluid. The reaction was followed on a 96 well microtiter plate reader using an excitation an emission wavelength of 355 nm and 538 nm respectively at 37° C. The reaction was monitored for a period of 1 h and plotted using the KALEIDAGRAPH software.

The assay in wound fluid gave similar results for *S. pyogenes*, but *Pseudomnonas* did not have any activity above the background. The same results were obtained when the assay was repeated with bacterial supernatant.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for detecting the presence or absence of a proteinase in a sample, wherein the presence of the proteinase is indicative of the presence of bacteria selected from the group consisting of *Streptococcus pyogenes, Pseudomonas aeruginosa, Enterococcus faecalis, Proteus mirabilis* and combinations thereof, in the sample, wherein the method comprises the steps of:
   a) contacting the sample with a detectably labeled substrate, wherein the substrate comprises a cationic anti-microbial peptide variant consisting essentially of either SEQ ID NO: 1 or SEQ ID NO: 2, wherein said peptide variant does not comprise SEQ ID NO:3, and wherein the peptide variant is degradable by a proteinase produced and/or secreted by said bacteria, under conditions that result in the degradation of the peptide variant by the proteinase, wherein degradation of the peptide variant results in a detectable signal; and
   b) detecting the resulting signal indicative of the peptide variant degradation, wherein degradation of the peptide variant indicates the presence of the bacterial proteinase in the sample.

2. The method of claim 1, wherein said sample is selected from the group consisting of a wound fluid and a body fluid.

3. The method of claim 1, wherein said peptide variant is on a solid support.

4. The method of claim 3, wherein the solid support comprises a material suitable for sterilization prior to contact with the sample.

5. The method of claim 3, wherein said solid support is selected from the group consisting of a wound dressing, a container for holding body fluids, a disk, a scope, a filter, a lens, foam, cloth, paper, a suture, and a swab.

6. The method of claim 5, wherein said container for holding body fluids is selected from the group consisting of a urine collection bag, a blood collection bag, a plasma collection bag, a test tube, a catheter, and a well of a microplate.

7. The method of claim 2 wherein the sample is wound fluid and detection of the presence of the proteinase in wound fluid is indicative of the presence of said bacteria in the wound.

8. The method of claim 7 wherein the presence of said bacteria in the wound fluid is an indication of a wound infection.

9. The method of claim 2 wherein the body fluid is selected from the group consisting of: blood, urine and sputum.

10. The method of claim 9 wherein the presence of the proteinase in the body fluid is indicative of the presence of said bacteria in the blood, urine or sputum.

11. A method comprising:
   a) contacting a body fluid with a detectably labeled substrate, wherein the substrate comprises a cationic anti-microbial peptide variant consisting essentially of either SEQ ID NO: 1 or SEQ ID NO: 2, wherein said peptide variant does not comprise SEQ ID NO:3, which is degradable by a proteinase produced and/or secreted by one or more pathogenic bacteria species, under conditions that result in the degradation of the peptide variant by the proteinase, wherein degradation of the peptide variant results in a detectable signal; and
   b) detecting the resulting signal.

12. The method of claim 11, wherein the body fluid is selected from the group consisting of wound fluid, blood, urine and sputum.

13. The method of claim 12, wherein the body fluid is wound fluid.

14. The method of claim 11, wherein the pathogenic bacteria species is selected from the group consisting of *Streptococcus pyogenes, Pseudomonas aeruginosa, Enterococcus faecalis, Proteus mirabilis* and combinations thereof.

15. The method of claim 14, wherein the pathogenic bacteria species is *Streptococcus pyogenes*.

16. A method comprising:
   a) contacting a sample contacted by body fluid with a detectably labeled substrate, wherein the substrate comprises a cationic anti-microbial peptide variant consisting essentially of either SEQ ID NO: 1 or SEQ ID NO: 2, wherein said peptide variant does not comprise SEQ ID NO:3, which is degradable by a proteinase produced and/or secreted by one or more pathogenic bacteria species, under conditions that result in the degradation of the peptide variant by the proteinase, wherein degradation of the peptide variant results in a detectable signal; and
   b) detecting the resulting signal.

17. The method of claim 16, wherein the body fluid is selected from the group consisting of wound fluid, blood, urine and sputum.

18. The method of claim 16, wherein the pathogenic bacteria species is selected from the group consisting of *Streptococcus pyogenes, Pseudomonas aeruginosa, Enterococcus faecalis, Proteus mirabilis* and combinations thereof.

19. The method of claim 18, wherein the pathogenic bacteria species is *Streptococcus pyogenes*.

20. The method of claim 16, wherein the sample is selected from the group consisting of a wound dressing, a container for holding body fluids, a disk, a scope, a filter, a lens, foam, cloth, paper, a suture, and a swab.

* * * * *